United States Patent [19]

Brown et al.

[11] Patent Number: 5,082,984
[45] Date of Patent: Jan. 21, 1992

[54] DUAL FUNCTION CATALYST AND ISOMERIZATION THEREWITH

[75] Inventors: Lawrence M. Brown deceased, late of Lawrenceville, N.J., by Dorothy M. Brown, Administratrix; Tracy J. Huang, Lawrenceville, N.J.

[73] Assignee: Mobil Oil Corp., Fairfax, Va.

[21] Appl. No.: 664,243

[22] Filed: Mar. 4, 1991

Related U.S. Application Data

[62] Division of Ser. No. 471,462, Jan. 29, 1990, Pat. No. 5,028,573.

[51] Int. Cl.$^5$ .............................................. C07C 5/22
[52] U.S. Cl. ..................................... 585/481; 585/477; 585/482
[58] Field of Search ...................... 585/477, 481, 482

[56] References Cited

U.S. PATENT DOCUMENTS

| | | | |
|---|---|---|---|
| 3,578,723 | 5/1971 | Bowes et al. | 260/672 |
| 3,856,872 | 12/1974 | Morrison | 260/668 A |
| 3,965,207 | 6/1976 | Weinstein | 260/671 M |
| 3,965,208 | 7/1976 | Butter et al. | 260/671 M |
| 3,965,209 | 6/1976 | Butter et al. | 260/671 M |
| 3,965,210 | 6/1976 | Chin-Chiun Chu | 260/671 M |
| 4,101,595 | 7/1978 | Chen et al. | 260/668 A |
| 4,117,026 | 9/1978 | Haag et al. | 585/475 |
| 4,159,282 | 6/1979 | Olson et al. | 585/481 |
| 4,163,028 | 7/1979 | Tabak et al. | 585/481 |
| 4,351,979 | 9/1982 | Chester et al. | 585/481 |
| 4,402,866 | 9/1983 | Sihabi | 502/77 |

Primary Examiner—Patrick P. Garvin
Assistant Examiner—E. D. Irzinski
Attorney, Agent, or Firm—Alexander J. McKillop; Charles J. Speciale; Dennis P. Santini

[57] ABSTRACT

A dual function composite catalyst for isomerizing an isomerization feed containing an aromatic $C_8$ mixture of ethyl benzene and xylene, comprises (a) a crystalline aluminosilicate zeolite having a low acid activity as measured by an alpha value of from 0.02 to 11, an average crystal size of not more than 0.4 microns for at least 50% by weight of the crystals, a silica to alumina ratio of at least about 12, a constraint index of about 1 to 12, a xylene sorption capacity greater than 1 gram per 100 grams of zeolite, and an ortho-xylene sorption time for 30 percent of said capacity less than 10 minutes, said sorption capacity and sorption time being measured at 120° C. and a xylene pressure of 4.5±0.8 mm of mercury, and (b) a supported metal of Group VIII of the Periodic Table having a high hydrogenation/dehydrogenation activity to provide the catalyst with a dehydrogenation activity of at least 10. The catalyst has an alpha value of 0.005 to 3.

12 Claims, 2 Drawing Sheets

DUAL FUNCTION CATALYST AND ISOMERIZATION THEREWITH

This is a division of copending application Ser. No. 471,462, filed on Jan. 29, 1990, now U.S. Pat. No. 5,028,573.

BACKGROUND OF THE INVENTION

Since the announcement of the first commercial installations of Octafining in Japan in June, 1958, this process has been widely installed for the supply of p-xylene See "Advances in Petroleum Chemistry and Refining", volume 4, page 433 (Interscience Publishers, New York 1961) That demand for p-xylene has increased at remarkable rates, particularly because of the demand for terephthalic acid to be used in the manufacture of polyesters.

Typically, p-xylene is derived from mixtures of $C_8$ aromatics, separated from such raw materials as petroleum naphthas, particularly reformates, usually by selective solvent extraction. The $C_8$ aromatics in such mixtures and their properties are:

|  | Freezing Point °F. | Boiling Point °F. | Density Lbs./U.S. Gal. |
|---|---|---|---|
| Ethylene benzene | −139.0 | 277.1 | 7.26 |
| P-xylene | 55.9 | 281.0 | 7.21 |
| M-xylene | −54.2 | 292.0 | 7.23 |
| O-xylene | −13.3 | 292.0 | 7.37 |

Principal sources of the mixtures of $C_8$ aromatics are catalytically reformed naphthas and pyrolysis distillates. The $C_8$ aromatic fractions from these sources vary quite widely in composition but will usually be in the range 10 to 60 wt. % ethyl benzene (EB) with the balance, xylenes, being divided approximately 50 wt. % meta and 25 wt. % each of para and ortho.

In turn, calculated thermodynamic equilibria for the $C_8$ aromatic isomers at Octafining conditions are:

| Temperature | 850° F. |
|---|---|
| Wt. % Ethyl benzene | 8.5 |
| Wt. % para xylene | 22.5 |
| Wt. % meta xylene | 48.0 |
| Wt. % ortho xylene | 21.5 |
| TOTAL | 100.0 |

An increase in temperature of 50° F. will increase the equilibrium concentration of ethyl benzene by about 1 wt. %, will not change the ortho-xylene, and will decrease the para and meta xylenes each by about 0.5 wt. %.

Individual isomer products may be separated from the naturally occurring mixtures by appropriate physical methods. Ethyl benzene may be separated by fractional distillation although this is a costly operation. Ortho xylene may be separated by fractional distillation and is so produced commercially. Para xylene is separated from the mixed isomer by fractional crystallization.

As commercial use of para and ortho xylene has increased there has been interest in isomerizing the other $C_8$ aromatics toward an equilibrium mix and thus increasing yields of the desired xylenes.

The Octafining process operates in conjunction with the product xylene or xylenes separation processes. A virgin $C_8$ aromatics mixture is fed to such a processing combination in which isomers emerging from the product separation steps are then charged to the isomerizer unit and the effluent isomerizate $C_8$ aromatics are recycled to the product separation steps. The composition of isomerizer feed is then a function of the virgin $C_8$ aromatic feed, the product separation unit performance, and the isomerizer performance.

The isomerizer unit itself is most simply described as a single reactor catalytic reformer As in reforming, the catalyst contains a small amount of platinum and the reaction is carried out in a hydrogen atmosphere.

| Process Conditions | |
|---|---|
| Reactor Pressure | 175 to 225 PSIG |
| Reactor Inlet Temperature Range | 830–900° F. |
| Heat of Reaction | Nil |
| Liquid Hourly Space Velocity | 0.6 to 1.6 Vol/Vol/Hr. |
| Number of Reactors, Downflow | 1 |
| Catalyst Bed Depth, Feet | 11 to 15 |
| Catalyst Density, Lb/Cu. Ft. | 38 |
| Recycle Circulation, Mols Hydrogen/Mol Hydrocarbon Feed | 7.0 to 14.0 |
| Maximum Catalyst Pressure Drop, PSI | 20 |

It will be seen that the Octafining system is adapted to produce maximum quantities of p-xylene from a mixed $C_8$ aromatic feed containing all of the xylene isomers plus ethyl benzene. The key to efficient operation for that purpose is in the isomerizer which takes crystallizer effluent lean in p-xylene and converts the other xylene isomers in part to p-xylene for further recovery at the crystallizer.

Among the xylene isomerization processes available in the art, Octafining has been unique in its ability to convert ethyl benzene. Other xylene isomerization processes have required extremely expensive fractionation to separate that component of $C_8$ aromatic fractions. As will be seen from the table of properties above, the boiling point of ethyl benzene is very close to those of p- and m-xylene. Complete removal of ethyl benzene from the charge is impractical. The usual expedient for coping with the problem is an ethyl benzene separation column in the isomerizer-separator loop when using catalysts other than those characteristic of Octafining It will be seen that Octafining does not have this expensive auxiliary to prevent build up of ethyl benzene in the loop. This advantageous feature is possible because the Octafining catalyst converts ethyl benzene.

The Octafining process has been extensively discussed in the literature, for example:
1. Pitts, P. M., Connor, J. E., Luen, L. N., *Ind. Eng. Chem.*, 47, 770 (1955).
2. Fowle, M. J., Bent, R. D., Milner, B. E., presented at the Fourth World Petroleum Congress, Rome, Italy, June 1955.
3. Ciapetta, F. G., U.S. Pat. No. 2,550,531 (1951).
4. Ciapetta, F. G., and Buck, W. H., U.S. Pat. No. 2,589,189.
5. Octafining process, Process Issue, Petroleum Refinery, 1st Volume 38 (1959), No. 11, Nov., page 278.

A typical charge to the isomerizing reactor (effluent of the crystallizer) may contain 17 wt. % ethyl benzene, 65 wt. % m-xylene, 11 wt. % p-xylene and 7 wt % o-xylene. The thermodynamic equilibrium varies slightly with temperature. The objective in the isomerization reactor is to bring the charge as near to theoretical equilibrium concentrations as may be feasible, consistent with reaction times which do not give extensive cracking and disproportionation.

Ethyl benzene reacts through ethyl cyclohexane to dimethyl cyclohexanes which in turn equilibrate to xylenes. Competing reactions are disproportionation of ethyl benzene to benzene and diethyl benzene, hydrocracking of ethyl benzene to ethylene and benzene and hydrocracking of the alkyl cyclohexanes.

The rate of ethyl benzene approach to equilibrium concentration in a $C_8$ aromatic mixture is related to effective contact time. Hydrogen partial pressure has a very significant effect on ethyl benzene approach to equilibrium. Temperature change within the range of Octafining conditions (830° to 900° F.) has but a very small effect on ethyl benzene approach to equilibrium.

Concurrent loss of ethyl benzene to other molecular weight products relates to % approach to equilibrium. Products formed from ethyl benzene include $C_6$+naphthenes, benzene from cracking, benzene and $C_{10}$ aromatics from disproportionation and total loss to other than $C_8$ molecular eight. $C_5$ and light hydrocarbon by-products are also formed.

The three xylenes isomerize much more selectively than does ethyl benzene, but they do exhibit different rates of isomerization and hence, with different feed composition situations the rates of approach to equilibrium vary considerably.

Loss of xylenes to other molecular weight products varies with contact time. By-products include naphthenes, toluene, $C_9$ aromatics and $C_5$ and lighter hydrocracking products.

Ethyl benzene has been found responsible for a relatively rapid decline in catalyst activity and that effect is proportional to its concentration in a $C_8$ aromatic feed mixture. It has been possible then to relate catalyst stability (or loss in activity) to feed composition (ethyl benzene content and hydrogen recycle ratio) so that for any $C_8$ aromatic feed, desired xylene products can be made with a selected suitably long catalyst use cycle.

A relatively recent development in this art involves the use of a unique class of zeolite catalysts for isomerization of xylenes in a p-xylene recovery loop. The zeolite catalysts designated ZSM-5 and ZSM-12 as well as other zeolites having like properties will induce extensive disproportionation of ethyl benzene at very low loss of xylene by that reaction, all as described in U.S. Pat. No. 3,856,872, Morrison, dated Dec. 24, 1974. As shown in that patent, isomerization of $C_8$ aromatics with such zeolite catalysts avoids buildup of ethyl benzene in the loop by converting that compound to lower boiling benzene and higher boiling polyalkyl benzenes which are separated by inexpensive splitters and strippers in the loop.

Another solution to the ethyl benzene problem, in addition to Octafining and the Morrison process, has been to supply xylenes which are free of ethyl benzene. The favored sources of such pure xylene streams are techniques for conversion of toluene as by disproportionation and methylation.

Disproportionation of toluene can be accomplished with porous acid solid catalysts to yield benzene and a mixture of xylenes. The product is, of course, free of ethyl benzene. See, for example, U.S. Pat. No. 3,578,723, Bowes and Wise, dated May 11, 1971.

Reaction of toluene with a methylating agent such as methanol produces xylenes and higher boiling polymethyl benzenes which are readily separated from the product xylenes and may be reacted with toluene to form additional xylenes by transalkylation reactions. Recent developments in synthesis of xylenes by methylation of toluene have been constituted by provision of catalysts which favor production of p-xylene such that the product xylene streams contains a proportion of p-xylene much in excess of the thermodynamic equilibrium value, thereby facilitating separation of p-xylene at reduced cost. These catalysts having enhanced capability for formation of p-xylene generally manifest a restriction of rate of diffusion of xylenes other than the para isomer, a property conveniently measured as rate of diffusion of o-xylene as set out more fully hereinafter. Patents describing methods for preparation and use of such catalysts include: U.S. Pat. No. 3,965,207 to Weinstein, U.S. Pat. No. 3,965,208 to Butter & Kaeding, U.S. Pat. No. 3,965,209 to Butter & Young, and U.S. Pat. No. 3,965,210 to Chu.

U.S. Pat. No. 4,159,282 to Olson et al describes a xylene isomerization process in which a specified crystalline aluminosilicate zeolite characterized by a crystal size of at least about 1 micron is employed as an isomerization catalyst. In a more specific embodiment, the reaction is carried out with a crystalline aluminosilicate catalyst having a bimodal crystal size distribution generally falling in two ranges, less than about 1 micron and greater than about 1 micron with the latter being in major proportion.

The zeolite preferably has a defined xylene sorption capacity of greater than 1 gram/100 grams of zeolite and a defined ortho-xylene sorption time for 30 percent of the sorption capacity of greater than 10 minutes, the sorption capacity and sorption time being measured at 120° C. and a xylene pressure of 4.5±0.8 mm of mercury. The defined sorption time is obtained by modifying the zeolite, such as by combining the zeolite with a difficultly reducible oxide, or by precoking or by steaming the catalyst. The original alkali metal of the zeolite may be replaced by ion exchange with other suitable ions of Groups IB to VIII of the Periodic Table. The process employs an ethyl benzene feed containing xylenes. Olson et al broadly state that they can process a mixture of $C_8$ aromatics, such as that derived from platinum reforming of a petroleum naphtha, to a mixture of reduced ethyl benzene content and increased content of paraxylene. The process, however, results in xylene loss, as shown by the various examples of Olson et al.

U.S. Pat. No. 4,163,028 to Tabak et al describes a xylene isomerization process in which a low acid activity catalyst, typified by zeolite ZSM-5 of low alumina content ($SiO_2/Al_2O_3$ of about 500 to 3000 or greater) and which may contain highly dispersed metals, such as platinum or nickel, is employed as an isomerization catalyst at a temperature of 800° F. or higher. The patent states that at these temperatures, ethyl benzene reacts primarily by dealkylation to benzene and ethane rather than by disproportionation to benzene, and hence is strongly decoupled from the catalyst acid function. Since ethyl benzene conversion thereby is less dependent on the acid function, a lower acidity catalyst can be used to perform the relatively easy xylene isomerization. The patent does not quantify or define the low acid activity of the catalyst or the dispersing or dehydrogenation activity of the dispersed metal. The process permits high conversion of ethyl benzene to benzene and it is stated in the patent to do so at little or no conversation of xylenes. All of the examples in the patent, however, show xylene loss. The process also is stated to be able to convert paraffin hydrocarbons.

U.S. Pat. No. 4,101,595 to Chen et al describes a process for converting ethyl benzene to para xylene which employs a dual function catalyst comprised of a shape selective moderate or low acid zeolite and a strong hydrogenation/dehydrogenation metal of Group VIII of the Periodic Table. The zeolite must have restricted diffusion of o-xylene as determined by a defined ortho-xylene sorption time for 30 percent of the sorption capacity of greater than 10 minutes, which can be achieved by using large crystals of, for example, zeolite ZSM-5 having average dimension of individual crystals about 0.5 microns and greater. This patent states that small crystal zeolites may be modified to show the restricted diffusion effect by techniques known to the art.

Chen et al further state that the zeolite should have a reduced acid function to minimize losses to hydrocracking. Chen et al disclose that this can be achieved by adding a catalyst poison to the charge or by treating the catalyst to reduce its activity by steaming, partial exchange with such cations as alkali metals, partial coking and like known deactivating methods. When operating without a catalyst poison in the charge, Chen et al state that the zeolite should be deactivated to a reduced activity, measured as alpha value, between 0.05 and 1.

The zeolites employed by Chen et al are stated to have unusually low alumina contents, that is, high silica to alumina ratios. The highest silica to alumina ratio disclosed by Chen et al is 200.

Chen et al state that the feed or charge can be a mixture of ethyl benzene and xylene isomers, and that the product stream can contain an increased xylene and decreased ethyl benzene content as compared with the charge. Chen et al state that a feed constituted by an approximately equilibrium mixture of ethyl benzene and the three xylene monomers can be passed to an ethyl benzene converter in which the ethyl benzene is converted in large measure to xylenes, including a proportion of p-xylene in excess of equilibrium. The various examples of Chen et al employ a charge a ethyl benzene and no example shows a mixed charge of ethyl benzene with xylenes. The Chen et al examples for converting ethyl benzene employ a ZSM-5 crystalline having a 2 micron average crystal size and a silica/alumina mol ratio of 70.

SUMMARY OF THE INVENTION

An object of the present invention is to provide a new catalyst for the isomerization of xylene.

Another object of the present invention is to provide a new catalyst for the isomerization of a feed containing an aromatic $C_8$ mixture of ethyl benzene and xylene which does not result in xylene loss and which can bring about xylene gain.

A further object of the present invention is to provide an isomerization process for isomerizing xylene employing the catalyst of the present invention.

Additional objects and advantages of the present invention will be set forth in part in the description which follows and in part will be obvious from the description or can be learned by practice of the invention. The objects and advantages are achieved by means of the processes, instrumentalities and combinations particularly pointed out in the appended claims.

To achieve the foregoing objects and in accordance with its purpose, the present invention provides a dual function composite catalyst for isomerizing an isomerization feed containing an aromatic $C_8$ mixture of ethyl benzene and xylene, comprising:

(a) a crystalline aluminosilicate zeolite having a low acid activity as measured by an alpha value of from about 0.02 to about 11, an average crystal size of not more than about 0.4 microns for at least 50% by weight of the crystals, a silica to alumina ratio of at least about 12, a constraint index of about 1 to 12, a xylene sorption capacity greater than 1 gram per 100 grams of zeolite, and an ortho-xylene sorption time for 30 percent of said capacity less than 10 minutes, said sorption capacity and sorption time being measured at 120° C. and a xylene pressure of 4.5±0.8 mm of mercury, and (b) a supported metal of Group VIII of the Periodic Table having a high hydrogenation/dehydrogenation activity to provide the catalyst with a dehydrogenation activity of at least 10, and (c) the catalyst having an alpha value of 0.005 to 3.

The dual functional xylene isomerization catalyst of the present invention selectively isomerizes ethyl benzene (EB) to para-rich xylene. It has the ability to isomerize $C_8$ aromatic streams in a single reactor with the production of a net gain of xylenes, the magnitude of which increases with increasing concentration of ethyl benzene in the feedstock. These processing characteristics are observed with unextracted feedstocks as well as with those from which paraffins have been removed by means of extraction.

The catalyst of the present invention contains a zeolite of low acid activity as the acidic component, preferably ZSM-5, and a supported metal of high specific activity as the hydrogenation/dehydrogenation component.

The catalyst is preferably an intimate mixture of the powders of the two components which mixture of powders is then formed into larger particles such as by extrusion or pelleting. The catalyst may also be a mixture of larger particles composed of particles of zeolite and particles of supported metal, such as extrudate or pelleted particles of each. The support for the metal is preferably alumina, but it may also be another inorganic oxide such as silica, silica-alumina, titania, magnesia, boria or zirconia.

The required acidic activity of the composite catalyst is 0.005 to 3 alpha, preferably 0.05 to 2.5 alpha, and most preferably 0.05 to 2.2, based on the alpha value for hexane cracking at 1000° F. This range of acidities can be achieved with a zeolitic component whose alpha value ranges from 0.02 to 11, and preferably from 0.1 to 5.

The zeolite component of the present invention preferably is either a high silica form or a sodium-hydrogen form prepared by means of partial ion-exchange of a hydrogen form of normal $SiO_2/Al_2O_3$ ratio, preferably with a solution of sodium bicarbonate. Steaming is an alternative procedure for reducing the acidity of the zeolite.

The preferred acidic zeolite component is ZSM-5, which has a constraint index of 1 to 12. However, the acidic zeolite component may also be another member of the group of zeolites, provided that its pore diameter does not greatly exceed that of ZSM-5, and provided that its constraint index is not much lower, which is the case, for example, for either ZSM-11 or ZSM-12.

The hydrogenation/dehydrogenation component of the catalyst of the present invention comprises at least one metal selected from Group VIII of the Periodic Table, for example, Pt, Pd, Ir, Rh, Ru. It may also include an additional metal selected from Group VIIA, for example, Re; or Group IVB, for example, Sn. The metal may be incorporated in the catalyst by means of impregnation of the zeolite, by impregnation of a support, or by impregnation of a composite of the zeolite and support.

The metal-content of the catalyst of the present invention preferably is 0.05 to 1.0 wt %, and more preferably 0.1 to 0.4 wt based on the weight of the composited catalyst.

Impregnation of the metal is accomplished with high dispersion to ensure a dehydrogenation activity of at least 10, preferably at least 25, based on the rate constant per gram of Pt for dehydrogenation of cyclohexane to benzene at 600° F. and a partial pressure of 0.1 atm.

The catalyst of the present invention is selective for the hydroisomerization of ethyl benzene to para-rich xylenes as a result of its high dehydrogenation activity, but not for dealkylation of ethyl benzene. Further, because of the low activity of the catalyst, xylene losses arising from hydrocracking, disproportionation and transalkylation are relatively small. Thus, the catalyst of the present invention has the ability to produce a net gain of xylenes over a range of ethyl benzene-conversions with a variety of $C_8$ aromatic streams that differ greatly in their ethyl benzene concentration. Although some xylenes are lost by means of hydrocracking, the yield of xylenes from the isomerization of ethyl benzene is more than sufficient to offset those losses. Thus, the catalyst of the present invention can produce higher xylene yields than those obtained in other known processes. The product xylenes produced by employing the catalyst and process of the present invention usually contain at least an equilibrium quantity of the paraisomer.

The present invention also provides a process for isomerizing an isomerization feed containing an aromatic $C_8$ mixture of ethyl benzene and xylene by contacting the feed, under conversion conditions, with the catalyst of the present invention.

Preferably, the conversion is performed at a temperature between 700° and 900° F., such as 750° to 800° F., at a pressure between 100 and 1000 psig, such as 150 to 300 psig, using a feed weight hourly space velocity (WHSV) (weight of feed per hour/weight of catalyst) between about 1 and about 50. The WHSV is based on the weight of the catalyst composition, i.e., total weight of active catalyst and, if employed, binder therefor. Preferably, but not necessarily the isomerization is effected in the presence of hydrogen. Hydrogen may be present in the isomerization zone in an amount between about 0 and about 10 mols, preferably between about 1 and about 5 mols, of hydrogen per mole of hydrocarbon. The above process conditions include operation in liquid vapor or mixed phase.

It is to be understood that both the foregoing general description and the following detailed description are exemplary and explanatory, but are not restrictive of the invention.

DISCUSSION OF PREFERRED EMBODIMENTS

The catalyst and process of the present invention are adapted to produce para dialkyl benzenes from monoalkyl benzenes of eight to ten carbon atoms, i.e. having a single alkyl side chain of two to four carbon atoms. Preferably the alkyl substituent is normal alkyl, it being found that branched side chains are more subject to hydrocracking than are straight side chains. The feed may be constituted by such monoalkyl benzenes or may be a mixture of mono alkyl benzenes with other substituted aromatics as in the preferred embodiment for conversion of a $C_8$ aromatic fraction containing ethyl benzene and the three xylene isomers.

In general, any aromatic $C_8$ mixture containing ethyl benzene and xylene may be used as feed to the process of this invention. Generally, such mixture will have an ethyl benzene content in the approximate range of 5 to 60 weight percent, an ortho xylene content in the approximate range of 0 to 35 weight percent, a meta xylene content in the approximate range of 20 to 95 weight percent and a para xylene range of 0 to 15 weight percent. The feed in addition to above aromatic $C_8$ mixture may contain non-aromatic hydrocarbons, i.e., naphthenes and paraffins in an amount up to 30 weight percent. In a preferred embodiment, the invention provides means to process a mixture of $C_8$ aromatics such as that derived from platinum reforming of a petroleum naphtha to a mixture of reduced ethyl benzene content and increased content of para-xylene.

The catalyst of the present invention is especially suitable for the isomerization of $C_8$ aromatic streams that contain about 10 to 60 wt. % ethyl benzene, and preferably 25 to 60 wt. % ethyl benzene. This range spans the range of ethyl benzene concentrations of streams that are derived from a reformer and a pyrolysis gasoline unit. Also, the catalyst has high activity for cracking of normal and branched paraffins of the type present in unextracted $C_8$ aromatic streams.

The charge hydrocarbons are admixed with hydrogen in a molar proportion of about 1 to about 10 mols of hydrogen per mol of hydrocarbons and contacted with the dual functional catalyst at 700° to 900° F. and pressure of 100 to 1000 pounds per square inch (psig). Space velocity can vary with severity of other conditions and the feed weight hourly space velocity (WHSV) will generally be about 1 to 50. The WHSV is based on the weight of catalyst composition, i.e., the total weight of active catalyst and, if used, binder therefor.

The composite catalyst of the present invention is a combination of a crystalline aluminosilicate zeolite having a silica/alumina ratio of at least 12, a constraint index between 1 and 12 and a crystal density of not less than 1.6 grams per cubic centimeter with a noble metal of Group VIII of the Periodic Table.

The zeolite component of the catalyst of the present invention has an average crystal size of not more than about 0.4 microns for at least 50% by weight of the crystals.

It is well known that the crystal size of zeolite crystals having a silica to alumina ratio of at least about 12 and a constraint index within the range of 1 to 12 reflects the diffusion properties of the zeolite, which, in turn, reflects the xylene sorption characteristics of the zeolite. Such a zeolite, in unmodified form, as crystallized with a minimum crystal dimension of less than about 0.5 micron, has a xylene sorption capacity greater than 1 gram/100 grams of zeolite measured under specified conditions and an ortho-xylene sorption time for 30 percent of xylene sorption capacity, measured under the same specified conditions, (measured at 120° C. and a xylene pressure of 4.5±0.8 mm of mercury) of considerably less than 10 minutes. Such a catalyst in the past has been found to be unsuitable for use as a catalyst in the selective product of para dialkyl substituted benzenes in which the alkyl group contains from 1 to 4 carbon atoms. See U.S. Pat. No. 4,117,026 to Haag et al and U.S. Pat. No. 4,101,595 to Chen et al.

In order to achieve selective formation of the desired para dialkyl-substituted benzene, the prior art has modified the diffusivity of the above-noted type zeolite. Thus, considering selective production of para-xylene, the prior art has taught that such is obtained if ortho and meta xylene, produced within the zeolite crystal, can isomerize to para-xylene at a rate which is greater than their diffusion out of the zeolite pores.

In order to achieve what was considered by the prior art to be a requisite diffusivity, the prior art modified the zeolite prior to use by a variety of techniques. In one such technique, the zeolite was combined with a small amount, generally about 2 to 30 weight percent, of a difficulty reducible oxide, such as oxides of antimony, boron, phosphorous, magnesium or combinations thereof. Prior modifications of the zeolite could also suitably be effected by precoking to deposit at least about 1 weight percent of coke thereon. Another means of achieving the diffusivity required by the prior art was the use of large crystal size zeolites having a minimum crystal dimension of greater than about 0.5 micron, generally 1 to 20 microns, and particularly 1 to 6 microns. In a preferred embodiment, a large crystal size zeolite was modified by precoking or combination with a difficulty reducible oxide.

As a result of the above modifications and/or the use of a large crystal size zeolite, the zeolites had a xylene sorption capacity greater than 1 gram/100 grams of zeolite measured under specified test conditions and an o-xylene sorption time greater than 10 minutes for 30 percent of the total capacity of the zeolite for sorbed xylene at equilibrium under the same specified test conditions of 120° C. and a xylene pressure of 4.5±0.8 mm of mercury.

In accordance with the present invention, it has been discovered surprisingly that if both the acid activity of the catalyst as measured by alpha value and the dehydrogenation activity of the catalyst are suitably selected, zeolites which do not show the restricted diffusivity required by the prior art can be used for the isomerization of $C_8$ aromatics with a net xylene gain.

Thus, in the present invention, the average crystal size of the zeolites is not more than about 0.4 microns for at least 50% by weight of the zeolite crystals Such zeolites have a xylene sorption capacity greater than 1 gram/100 grams of zeolite measured under specified test conditions and an ortho-xylene sorption time for 30 percent of xylene sorption capacity of less than 10 minutes, measured at the same specified test conditions of 120° C. and a xylene pressure of 4.5±0.8 mm of mercury. Moreover, the zeolites which are used in the present invention do not undergo any modifications which bring the above ortho-xylene sorption time to greater than 10 minutes, and thus when used in the present invention have the above ortho-xylene sorption time of less than 10 minutes, preferably 8 minutes or less, such as five minutes or less. Still more preferably, the ortho-xylene sorption time is three minutes or less, such as about 1.3 minutes or less.

Examples of such zeolites are an HZSM-5 which has an average crystal size of about 0.2 microns to 0.4 microns, such as 0.4 microns, and an HZSM-5 which has an average crystal size of 0.01 to 0.05 microns, such as about 0.03 microns.

In assessment of zeolite crystal size, conventional scanning electron microscopy (SEM) techniques can be used, with the minimum crystal dimension of a given crystal being taken as the dimension of reference The zeolites used in the present invention in substantial proportion thus are essentially characterized by a minimum crystal dimension of less than about 0.4 micron. Generally, the amount of zeolite of such crystal size will be present in predominate proportion, i.e., in an amount exceeding 50 wt. %, and preferably may constitute up to 100 weight percent of the total zeolite employed.

The measurements of hydrocarbon sorption capacities and rates are conveniently carried out gravimetrically in a thermal balance. In particular, it has been found that an equilibrium sorption capacity of xylene, which can be either para, meta, ortho or a mixture thereof, preferably para-xylene since this isomer reaches equilibrium within the shortest time of at least 1 gram per 100 grams of zeolite measured at 120° C. and a xylene pressure of 4.5±0.8 mm of mercury and an ortho-xylene sorption time for 30 percent of said capacity of less than 10 minutes (at the same conditions of temperatures and pressure) can be used in order to achieve the desired selective production of para dialkyl substituted benzenes, and particularly para-xylene.

It has been found that zeolites exhibiting very high selectivity for para-dialkylbenzene production require a very long time up to and exceeding a thousand minutes to sorp o-xylene in an amount of 30% of total xylene sorption capacity. For those materials it is more convenient to determine the sorption time for a lower extent of sorption, such as 5%, 10% or 20% of capacity, and to estimate the 30% sorption time by applying the following multiplication factors F as illustrated for 5% sorption:

$t_{0.3}F \cdot t_{0.05}$

| Percent of sorption capacity | Factor (F) to Estimate 30% Sorption Time |
|---|---|
| 5 | 36 |
| 10 | 9 |
| 20 | 2.2 |

The composite catalyst of the present invention has a reduced acid function to minimize losses, especially xylene losses, to hydrocracking, disproportionation and transalkylation.

The required acidic activity of the composite catalyst of the present invention is 0.005 to 3 alpha, and preferably 0.05 to 2.5 alpha, based on the alpha value for hexane cracking at 1000° F.

The alpha value reflects the relative activity of the catalyst with respect to a high activity silica-alumina cracking catalyst. To determine the alpha value as such term is used herein, n-hexane conversion is determined at about 1000° F. Conversion is varied by variation in space velocity such that a conversion level of 10 to 60 percent of n-hexane is obtained and converted to a rate constant per unit volume of zeolite and compared with that of silica-alumina catalyst which is normalized to a reference activity of 1000° F. Catalytic activity of the catalysts are expressed as multiple of this standard, i.e. the silica-alumina standard. The silica-alumina reference catalyst contains about 10 weight percent $Al_2O_3$ and remainder $SiO_2$. This method of determining alpha, modified as described above, is more fully described in the Journal of Catalysts, Volume VI, pages 278 to 287, 1966.

To achieve the desired alpha value for the composite catalyst, a zeolite component is employed whose alpha value is from 0.02 to 11, and preferably 0.1 to 5. Since the metal component and any support for the catalyst do not have any alpha value, to arrive at the overall alpha value of the composite catalyst, the alpha value for the zeolite is multiplied by the weight percent of the zeolite in the composite catalyst. Thus, for example, a catalyst containing 50 weight percent of a zeolite whose alpha value is 1.7 has an alpha value of 0.85.

Alpha values for the zeolite can be controlled to within the above range by suitable selection of the $SiO_2/Al_2O_3$ ratio of the zeolite, with higher ratios producing lower alpha values as well known in the art. It is also possible to provide a zeolite component which is reduced in acid activity as the result of subjecting the zeolite to one or more acidity reducing treatments, such as by steaming, partial exchange with such cations as alkali metals, and like known sodium exchange techniques. See, for example, U.S. Pat. Nos. 3,899,544, 3,960,978, 3,965,209, 4,105,537 and 4,224,141 for discussions of providing low acid activity zeolites.

Particularly preferred zeolites for use in the present invention are those zeolites having a silica to alumina ratio of at least about 12 and a constraint index within the approximate range of 1 to 12. These zeolites induce profound transformations of aliphatic hydrocarbons to aromatic hydrocarbons in commercially desirable yields and are generally highly effective in conversion reactions involving aromatic hydrocarbons. Although they have usually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30, and in some instances it is preferred to use zeolites having much higher silica to alumina mole ratios, i.e. 1600 and above. In addition, zeolites as otherwise characterized herein, but which are substantially free of aluminum, are found to be useful and even preferable in some instances. Such "high silica" or "highly siliceous" zeolites are intended to be included within this description.

The zeolites useful in the present invention, after activation, acquire an intracrystalline sorption capacity for normal hexane which is greater than that for water, i.e. they exhibit "hydrophobic" properties It is believed that this hydrophobic character is advantageous in the present invention.

The members of the class of zeolites useful herein have an intermediate pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering of the rings or pore blockage may render these zeolites ineffective.

Although 12-membered rings in theory would not offer sufficient constraint to produce advantageous conversions, it is noted that the puckered 12-ring structure of TMA (tetramethyl ammonium) offretite does show some constrained access. Other 12-ring structures may exist which may be operative for other reasons, and therefore, it is not the intention of the present invention to entirely judge the usefulness of the particular zeolite solely from theoretical structure considerations.

A convenient measure of the extent to which a zeolite provides controlled access to molecules of varying sizes to its internal structure is the Constraint Index of the zeolite. Zeolites which provide a highly restricted access to and egress from its internal structure have a high value for the Constraint Index, and zeolites of this kind usually have pores of small size, e.g. less than 5 Angstroms. On the other hand, zeolites which provide relatively free access to the internal zeolite structure have a low value for the Constraint Index, and usually pores of large size. The method by which Constraint Index is determined is described fully in U.S. Pat. No. 4,016,218, incorporated herein by reference for details of the method.

Constraint Index (CI) values for some typical materials, including some which are not within the purview of this invention, are:

| CI (at test temperature) | |
| --- | --- |
| ZSM-4 | 0.5 (316° C.) |
| ZSM-5 | 6-8.3 (371° C.-316° C.) |
| ZSM-11 | 5-8.7 (371° C.-316° C.) |
| ZSM-12 | 2.3 (316° C.) |
| ZSM-20 | 0.5 (371° C.) |
| ZSM-22 | 7.3 (427° C.) |
| ZSM-23 | 9.1 (427° C.) |
| ZSM-34 | 50 (371° C.) |
| ZSM-35 | 4.5 (454° C.) |
| ZSM-48 | 3.5 (538° C.) |
| ZSM-50 | 2.1 (427° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.6-2.0 (316° C.-399° C.) |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operations (conversion) and the presence or absence of binders. Likewise, other variables, such as crystal size of the zeolite, the presence of occluded contaminants, etc., may affect the Constraint Index. Therefore, it will be appreciated that it may be possible to so select test conditions, e.g. temperature, as to establish more than one value for the Constraint Index of a particular zeolite. This explains the range of Constraint Indices for some zeolites, such as ZSM-5, ZSM-11 and Beta.

It is to be realized that the above CI values typically characterize the zeolites shown in the table above (including some outside the scope of the present invention), but that such are the cumulative result of several variables useful in the determination and calculation thereof. Thus, for a given zeolite exhibiting a CI value within the range of 1 to 12, depending on the temperature employed during the test method within the range of 290° C. to about 538° C., with accompanying conversion between 10% and 60%, the CI may vary within the indicated range of 1 to 12. Likewise, other variables such as the crystal size of the zeolite, the presence of possibly occluded contaminants and binders intimately combined with the zeolite may affect the CI. It will accordingly be understood to one of ordinary skill in the art that the CI, as utilized herein, while affording a highly useful means for characterizing the zeolites of interest is approximate, taking into consideration the manner of its determination, with the possibility, in some instances, of compounding variable extremes. However, in all instances, at a temperature within the above-specified range of 290° C. to about 38° C., the CI will have a value for any given zeolite of interest for use in the present invention within the approximate range of 1 to 12.

The class of zeolites defined herein is exemplified by ZSM-5, ZSM-11, ZSM-12, ZSM-22, ZSM-23, ZSM-35, ZSM-48, Zeolite Beta and other similar materials.

ZSM-5 is more particularly described in U.S. Pat. No. 3,702,886 and U.S. Pat. No. Re. 29,948, the entire contents of which are incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-22 is more particularly described in U.S. Pat. Nos. 4,481,177, 4,556,477 and European Patent No. 102,716, the entire contents of each being expressly incorporated herein by reference.

ZSM-23 is more particularly described in U.S. Pat. No. 4,076,842, the entire contents of which are incorporated herein by reference.

ZSM-35 is more particularly described in U.S. Pat. No. 4,016,245, the entire contents of which are incorporated herein by reference.

ZSM-38 is more particularly described in U.S. Pat. No. 4,046,859, the entire contents of which are incorporated herein by reference.

Zeolite Beta is taught in U.S. Pat. No. 3,308,069 and is taught as a catalyst component for isomerization dewaxing in U.S. Pat. Nos. 4,419,220 and 4,501,926. These disclosures are also incorporated herein by reference.

ZSM-48 is more particularly described in U.S. Pat. No. 4,397,827 the entire contents of which are incorporated herein by reference.

The following description illustrates characteristics of zeolites useful in the present invention, using ZSM-48 as an example. This zeolite can be identified, in terms of moles of anhydrous oxides per 100 moles of silica, as follows:

$$(0-15)RN:(0-1.5)M_{2/n}O:(0.2)Al_2O_3:(100)SiO_2$$

wherein:

M is at least one cation having a valence n; and

RN is a $C_1$–$C_{20}$ organic compound having at least one amine functional group of $pK_a \leq 7$.

It is recognized that, particularly when the zeolite ZSM-48 composition contains tetrahedral framework aluminum, a fraction of the amine functional groups may be protonated. The doubly protonated form, in conventional notation, would be $(RNH)_2O$ and is equivalent in stoichiometry to $2\ RN + H_2O$.

The characteristic X-ray diffraction pattern of the synthetic zeolite ZSM-48 has the following significant lines:

| Characteristic Lines of ZSM-48 | |
| --- | --- |
| d (Angstroms) | Relative Intensity |
| 11.9 | W-S |
| 10.2 | W |
| 7.2 | W |
| 5.9 | W |
| 4.2 | VS |
| 3.9 | VS |
| 3.6 | W |
| 2.85 | W |

These values were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, 100 $I/I_o$, where $I_o$ is the intensity of the strongest line or peak, and d (obs.), the interplanar spacing in angstroms, corresponding to the recorded lines, were calculated. In the foregoing table the relative intensities are given in terms of the symbols W=weak, VS=very strong and W-S=weak-to-strong. Ion exchange of the sodium ion with cations reveals substantially the same pattern with some minor shifts in interplanar spacing and variation in relative intensity. Other minor variations can occur depending on the silicon to aluminum ratio of the particular sample, as well as if it has been subjected to thermal treatment.

The ZSM-48 can be prepared from a reaction mixture containing a source of silica, water, RN, an alkali metal oxide (e.g. sodium) and optionally alumina. The reaction mixture should have a composition, in terms of mole ratios of oxides, falling within the following ranges:

| REACTANTS | | BROAD | PREFERRED |
|---|---|---|---|
| $Al_2O_3/SiO_2$ | = | 0 to 0.02 | 0 to 0.01 |
| $Na/SiO_2$ | = | 0 to 2 | 0.1 to 1.0 |
| $RN/SiO_2$ | = | 0.01 to 2.0 | 0.05 to 1.0 |
| $OH-/SiO_2$ | = | 0 to 0.25 | 0 to 0.1 |
| $H_2O/SiO_2$ | = | 10 to 100 | 20 to 70 |
| $H+$ (added)/$SiO_2$ | = | 0 to 0.2 | 0 to 0.05 | wherein RN is a $C_1$-$C_{20}$ organic compound having at least one amine functional group of $pK_a \leq 7$. The mixture is maintained at 80°-250° C. until crystals of the material are formed. H+ (added) is moles acid added in excess of the moles of hydroxide added. In calculating H+ (added) and OH values, the term acid (H+) includes both hydronium ion, whether free or coordinated, and aluminum. Thus aluminum sulfate, for example, would be considered a mixture of aluminum oxide, sulfuric acid, and water. An amine hydrochloride would be a mixture of amine and HCl. In preparing the highly siliceous form of ZSM-48 no alumina is added. Thus, the only aluminum present occurs as an impurity in the reactants.

Preferably, crystallization is carried out under pressure in an autoclave or static bomb reactor, at 80° C. to 250° C. Thereafter, the crystals are separated from the liquid and recovered. The zeolite composition can be prepared utilizing materials which supply the appropriate oxide. Such materials include sodium silicate, silica hydrosol, silica gel, silicic acid, RN, sodium hydroxide, sodium chloride, aluminum sulfate, sodium aluminate, aluminum oxide, or aluminum itself. RN is a $C_1$-$C_{20}$ organic compound containing at least one amine functional group of $pk_a \leq 7$, as defined above, and includes such compounds as $C_3$-$C_{18}$ a primary, secondary, and tertiary amines, cyclic amines (such as piperidine, pyrolidine and piperazine), and polyamines such as $NH_2$—$C_nH_{2n}$—$NH_2$ wherein n is 4–12.

Turning from the above detailed description of ZSM-48 to the general class of zeolites useful in the present invention, the original cations which may be in/on the zeolite crystal framework can be subsequently replaced, at least in part, by calcination and/or ion exchange with another cation. Thus, the original cations are exchanged into a hydrogen or hydrogen ion precursor form or a form in which the original cation has been replaced by a metal of Groups II through VIII of the Periodic Table. Thus, for example, it is contemplated to exchange the original cations with ammonium ions or with hydronium ions. Catalytically active forms of these would include, in particular, hydrogen, rare earth metals, aluminum, manganese and other metals of Groups II and VIII of the Periodic Table.

It is to be understood that by incorporating by reference the foregoing patents to describe examples of specific members of the zeolite class useful in the present invention with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation by reference of the above-identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The zeolites described above for use in the present invention, when prepared in the presence of organic cations, are substantially catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this special type of zeolite However, the presence of these cations does appear to favor the formation of this type of zeolite which is used in the present invention. More generally, it is desirable to activate this type of zeolite by base exchange with ammonium salts followed by calcination in air at about 1000° F. for from about 15 minutes to about 24 hours.

Natural zeolites may sometimes be converted to this type zeolite by various activation procedures and other treatments such as base exchange, steaming, alumina extraction and calcination, alone or in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12, ZSM-22, ZSM-23, ZSM-35, ZSM-38 and ZSM-48, with ZSM-5 particularly preferred.

The zeolites used as catalysts in this invention may be in the hydrogen form or they may be base exchanged or impregnated to contain ammonium or a metal cation complement. It is desirable to calcine the zeolite after base exchange. The metal cations that may be present include any of the cations of the metals of Group I through VIII of the periodic table.

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In a preferred aspect of this invention, the zeolites useful as catalysts herein are selected from those having a crystal framework density, in the dry hydrogen form, of not substantially below about 1.6 grams per cubic centimeter. It has been found that zeolites which satisfy all three of the discussed criteria (i.e., a Constraint Index of 1 to 12, a silica to alumina ratio of at least about 12, and a crystal framework density of not substantially below about 1.6 g/cc) are most desired for use in the present invention. Therefore, the preferred catalysts of this invention are those comprising zeolites having a Constraint Index as defined above of about 1 to 12, a silica to alumina ratio of at least about 12 and a dried crystal density of not substantially less than about 1.6 grams per cubic centimeter. The dry density for known structures may be calculated from the number of silicon plus aluminum atoms per 1000 cubic Angstroms, as given, e.g., on page 19 of the article "Zeolite Structure" by W. M. Meier. This paper, the entire contents of which are incorporated herein by reference, is included in "Proceedings of the Conference on Molecular Sieves," (London, April, 1967) published by the Society of Chemical Industry, London, 1968.

When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, seems to be important as the locus of catalytic activity.

Crystal framework densities of some typical zeolites, including some which are not within the purview of this invention, are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |

| Zeolite | Void Volume | Framework Density |
|---|---|---|
| Y | .48 | 1.27 |

It is to be understood that the practice of the present invention is also applicable to isomorphs of the above-described crystalline aluminosilicate catalysts. For example, the aluminum may be replaced by elements such as gallium, and silicon by elements such as germanium.

A matrix binder can be employed with the zeolite component of the catalyst. The matrix material should be resistant to the temperature and other conditions employed in the process of the present invention. The matrix binder imparts greater resistance to the zeolite for the severe temperature, pressure and reactant feed stream velocity conditions encountered in the process of the present invention. The zeolite can be incorporated, combined, dispersed, or otherwise intimately admixed with the matrix binder in such proportions that the resulting composite will contain from 1% to 95% by weight and preferably from 10% to 70% by weight of the zeolite in the zeolite composite. A most preferred ratio is 65% by weight zeolite to 35% by weight matrix binder.

The term "matrix" includes inorganic compositions with which the zeolites can be incorporated, combined, dispersed, or otherwise intimately admixed with the catalyst wherein the matrix itself may be catalytically active or inactive, porous or nonporous. It is to be understood that the porosity of the composition employed as a matrix can be either inherent in the particular material or it can be introduced by mechanical or chemical means. Representative of matrices which can be employed include metals and alloys thereof, sintered metals, and sintered glass, asbestos, silicon carbide, aggregates, pumice, firebrick, diatomaceous earths, alumina and inorganic oxides. Inorganic compositions, especially those comprising alumina and those of a siliceous nature, are preferred. Of these matrices, inorganic oxides such as clay, chemically-treated clays, silica, silica alumina, etc., as well as alumina, are particularly preferred because of their superior porosity, attrition resistance and stability. Techniques for incorporating a zeolite into a matrix are known in the art and set forth in U.S. Pat. No. 3,140,253.

The catalyst of the present invention contains a supported metal of Group VIII of the Periodic Table having a high hydrogenation/dehydrogentation activity to provide the catalyst with a dehydrogenation activity of at least 10. The dehydrogenation activity (DA) is based on the rate constant per gram of Pt for dehydrogenation of cyclohexane to benzene at 600° F. and a partial pressure of 0.1 atm. Preferably, the dehydrogenation activity of the catalyst is at least 25, and more preferably is 50 or more. A dehydogenation activity of 100 or greater, such as 200, can be employed in the present invention.

By providing the catalyst with a high dehydrogenation activity, the catalyst is selective for hydroisomerization of ethyl benzene to para-rich xylenes, but not dealkylation of ethyl benzene.

The high dehydrogenation activity can be achieved by means well known in the art, and preferably is achieved by highly dispersing the Group VIII metal in the catalyst. The Group VIII metal can be supported on the zeolite itself, or on a separate support, or on a composite of the zeolite with a support, and can be incorporated in the catalyst by means of, for example, impregnation or ion exchange. The metal content of the Group VIII metal of the catalyst of the present invention preferably is 0.05 to 1.0 wt. % and more preferably 0.1 to 0.4 wt. %, based on the weight of the composited catalyst (zeolite, plus metal, plus support if any, plus binder if any).

The metal content preferably is provided on a support separate from the zeolite and separate from a composite of the zeolite with a support. When a separate support for the metal is employed, the resulting supported metal (support plus metal) preferably is employed in weight ratio of about 4:1 to about 1:4 with respect to zeolite. In especially preferred embodiments of the invention 1:1 physical mixtures of the zeolite and supported metal are employed. Suitable supports for the metal include $Al_2O_3$, silica, silica-alumina, titania, magnesia, boria, zirconia, or any of the other various binders mentioned above as being suitable for binding the zeolite component.

The improved conversion process of the present invention can be characterized generally as a process whereby a $C_8$ aromatic feed passes through a conversion zone containing the novel catalyst. However, even more improved results can be attained by modifying the noble metal/low acidity zeolite catalyst to its sulfide form. This modification can be achieved in two ways, i.e., by "presulfiding" the catalyst or by adding a sulfur-containing compound to the hydrocarbon feed In either case, the noble metal is converted to its sulfide form. Presulfiding, as used herein, can be performed by treating the noble metal/low acidity zeolite catalyst with, e.g., 0.05 to 10 vol. % $H_2S$ in $H_2$ at high temperatures, e.g., 350°–500° C., for a sufficient amount of time to convert the noble metal to the sulfide form. At 500° C. and 2 vol. % $H_2S$ in $H_2$, the presulfiding treatment should be carried out for about 2 hours to ensure complete reaction. This can be confirmed by testing the gaseous effluent with lead acetate paper.

The noble metal/low acidity zeolite catalyst can also be converted to the sulfide form by adding $H_2S$, $SO_2$ or an organic sulfur compound, such as dibenzothiophene, to the feed. Other suitable organic sulfur compounds include carbon disulfide, methylsulfide, thiophene, dimethylsulfide and dimethyldisulfide, etc. The sulfur compound should be added to the feed in an amount effective to convert the noble metal to its sulfide form i.e., from about 0.1 to 20 ppm (parts per million based on the total weight of the feed after sulfur addition) S (by wt.), preferably from 0.2 to 10 ppm S.

When the noble metal is converted to the sulfide form in accordance with this preferred aspect of the present invention, either by presulfiding the catalyst or by adding a sulfur-containing compound to the feed, the initial activity of Pt for hydrodealkylation of m-xylene to toluene is reduced, and xylene gain and selectivity are improved as compared to the unsulfided catalyst.

The following examples are given by way of illustration to further explain the principles of the invention. These examples are merely illustrative and are not to be understood as limiting the scope and underlying principles of the invention in any way. All percentages referred to herein are by weight unless otherwise indicated.

EXAMPLE I

Catalysts A to D, F and G according to the present invention were prepared by mixing a zeolite component with a metal component in the form of a $Pt/Al_2O_3$ catalyst, except for Catalyst A-2 where the metal component in the form of Pt was impregnated directly on the zeolite component. The zeolite component was either a high silica HZSM-5 of various $SiO_2/Al_2O_3$ ratios, a steamed HZSM-5, a sodium exchanged HZSM-5, or a HZSM-12, all having a crystal size within the range of the present invention and an ortho-xylene sorption time within the range of the present invention.

The various combinations of zeolite component and metal component used to prepare each catalyst, and various properties of the components and overall catalyst are set forth in Table 1 below.

Sodium-exchanged HZSM-5 Catalyst D was prepared by exchange with 0.5N sodium bicarbonate followed by back-exchange with $10^{-7}$N ammonium nitrate.

Pt-impregnation of the $Al_2O_3$ supports was carried out with $Pt(NH_3)_4Cl_2 \cdot H_2O$ via the incipient wetness technique.

Catalyst mixtures were prepared by mechanically grinding the components to powders that would pass through a 200-mesh screen. The powdered components were then mixed in the same grinder. The mixtures were pelleted and crushed to 14/30 mesh particles.

Catalyst activity was characterized by measurements of the alpha value of the zeolite and the dehydrogenation activity (DA) of the $Pt/Al_2O_3$ component. The DA represents the first order specific rate per gram of Pt for the $Pt/Al_2O_3$-catalyzed dehydrogenation of cyclohexane to benzene at 600° F. and a partial pressure of 0.1 atm.

The catalysts were pretreated in $H_2$ for two hours at 900° F. and 150 psig. After the temperature had been lowered to 750° F., the catalyst was presulfided to breakthrough with 450 ppm $H_2S$ in $H_2$ at 60–70 psig.

The ortho-xylene sorption time for 30 percent of the xylene sorption capacity was 1.3 minutes or less for the ZSM-5 catalysts having a crystal size of 0.03 microns, and less than 8 minutes for the ZSM-5 catalysts having a crystal size of 0.3 microns, with the sorption capacity and sorption time each being measured at 120° C. and a xylene pressure of 4.5±0.8 mm of mercury.

TABLE 1

| | | CATALYSTS | | | | | | |
|---|---|---|---|---|---|---|---|---|
| | | Catalyst | | Zeolite Component | | | | Metal Component |
| | | | | | Crystal Size | | | |
| | % Zeolite/% $Pt/Al_2O_3$ | Alpha | DA | Type | μ | Alpha | $SiO_2/Al_2O_3$ | % Pt-on-$Al_2O_3$ |
| A | 50/50 | 2.2 | 50 | HZSM-5 | ~0.3 | 4.5 | 2200 | 0.33 |
| A-1 | 50/50 | 2.2 | 25 | HZSM-5 | ~0.3 | 4.5 | 2200 | 0.18[a] |
| A-2 | 100% Pt-zeolite[b] | 2.2 | — | HZSM-5 | ~0.3 | 4.5 | 2200 | 0.6[b] |
| C | 50/50 | 0.85 | 50 | HZSM-5 | ~0.3 | 1.7 | 6000 | 0.33 |
| C-1 | 50/50 | 0.85 | 90 | HZSM-5 | ~0.3 | 1.7 | 6000 | 0.6 |
| G | 50/50 | 0.05 | 50 | HZSM-5 | ~0.3 | 0.1 | $10^5$ | 0.33 |
| B | 20/50 (30% $Al_2O_3$) | 2.2 | 50 | HZSM-5[c] | ~0.03 | 11.2 | 55 | 0.33 |

TABLE 1-continued

| | | CATALYSTS | | | | | | |
|---|---|---|---|---|---|---|---|---|
| | | | | Zeolite Component | | | | |
| | | Catalyst | | | Crystal Size | | | Metal Component |
| | % Zeolite/% Pt/Al$_2$O$_3$ | Alpha | DA | Type | μ | Alpha | SiO$_2$/Al$_2$O$_3$ | % Pt-on-Al$_2$O$_3$ |
| B-1 | 20/80 | 2.2 | 80 | HZSM-5 | ~0.03 | 11.2 | 55 | 0.03 |
| D | 50/50 | 0.01 | 50 | NaHZSM-5 | ~0.03 | 0.02 | 70 | 0.33 |
| F | 50/50 | 2.3 | 50 | HZSM-12 | <0.2$^d$ | 4.6 | 2200 | 0.33 |

$^a$Obtained with a mixture of Pt/Al$_2$O$_3$ containing 0.33% Pt (DA = 100) and 0.1% Pt (DA = 30).
$^b$Pt impregnated on binder-free zeolite.
$^c$Steamed for 24 hours at 1025° F. and 1 atm (100% steam).
$^d$Measured as the thickness of the plate of the platellet shaped crystals.

In the following examples, Catalysts A to D, F and G from Example 1 were used to isomerize various C$_8$ feeds in a fixed bed stainless steel reactor operating under pressure with no recycling. At start-up, the pressure was increased to 250 psig, and the feed admitted through the top of the reactor at a space velocity of 4 and a H$_2$/HC ratio of 10. At the same time, the temperature was increased at 5° C./min to the desired level. Initial conditions were then established and maintained for 24 hours before analyses of the product were made. The total product was cooled to ambient temperature and depressurized over a back pressure regulator to atmospheric pressure. The product was analyzed by gas chromatography.

In the following examples, product selectivities and yields were calculated by assuming that ethyl benzene (EB) is the sole source of the observed net xylene gain ($\Delta$xylene) and of all side-products, and that xylenes in the feed isomerized without a loss. While this approach suppressed the complexity of the reacting system, it provided a convenient basis for obtaining comparative data by which catalyst performance could be judged. In reality, some of the xylenes in the feed were hydrocracked. However, that loss was more than offset by the yield of xylenes formed by hydroisomerization of ethyl benzene.

Limiting values of the xylene selectivity and yield at extinction were calculated on the basis of assumed upper and lower limits for the selectivity with which recycled C$_8$-naphthenes (N) would isomerize to xylenes.

For the upper limit, it was assumed optimistically that those naphthenes would isomerize with 100% selectivity:

$$EB \rightarrow \Delta \text{ xylene} + \text{Naphthene} + \text{side products}$$

Thus, $$\text{Selectivity } (\%) = (100)(\Delta w_i)/(w_{EB}^0 - w_{EB}),$$

$$\text{Yield (wt \%)} = (\text{Selectivity}) \times (w_{EB}^0/100) + w_i^0,$$

where $\Delta w_i$ represents the difference between the product and feed in weight percent of component i, $w_{EB}^0$ is the weight percent of ethylbenzene in the feed, $w_{EB}$ is the weight percent of ethylbenzene in the product, and $w_i^0$ is the weight percent of component i in the feed. ($w_i$ is the weight percent of compound i in the product). Thus, for the total xylene selectivity and yield, $\Delta w_i = w_{\Delta xylene} + w_N$. Unless stated otherwise, the tabulated results are upper limits.

For the lower limit, it was assumed pessimistically that the recycled naphthenes and EB would isomerize with the same selectivity:

$$EB + N \rightarrow \Delta \text{ xylene} + \text{side products}$$

Thus, $$\text{Selectivity } (\%) = (100)(\Delta w_i)/(\Delta w_{EB} + \Delta w_N),$$

$$\text{Yield (wt \%)} = (\text{Selectivity}) \times (w_{EB}^0 + w_N^0)/100 + w_i^0.$$

In the following examples, APXE, % indicates the approach to equilibrium for para-xylene, AOXE, % indicates the approach to equilibrium for ortho-xylene and AEBE, % indicates the approach to equilibrium for ethyl benzene.

EXAMPLE 2

Catalyst G containing 50 wt. % of an HZSM-5 zeolite having an alpha of 0.1 (overall alpha of catalyst 0.05) and an SiO$_2$/Al$_2$O$_3$ ratio of 100,000 was employed to isomerize a model feed that contained 40% EB and 60% m-xylene at a temperature of 800° F. and an H$_2$/HC ratio of 5. Four runs (1 to 4) were made under varying conditions. The conditions and results are shown in Table 2 below.

TABLE 2

| | RUN NO. | | | |
|---|---|---|---|---|
| | 1 | 2 | 3 | 4 |
| P, psig | 200 | 200 | 200 | 250 |
| WHSV (catalyst) | 2.5 | 1.5 | 1 | 3 |
| EB Conversion, % | 35.6 | 42.8 | 50.2 | 38.6 |
| Xylene Gain, wt % | 4.2 | 5.0 | 7.7 | 4.4 |
| APXE, % | 94 | 106 | 110 | 89 |
| AOXE, % | 60 | 65 | 75 | 52 |
| B/$\Delta$EB, molar | 0.04 | 0.05 | 0.06 | 0.04 |
| Product Distribution, wt % | | | | |
| Light Gas | 1.4 | 2.0 | 1.6 | 0.9 |
| Non-aromatics (C$_6$ + C$_7$) | 2.1 | 2.6 | 2.2 | 2.4 |
| Aromatics (C$_6$, C$_7$, C$_9$, C$_{10}$) | 2.5 | 1.9 | 2.2 | 1.8 |
| Naphthenes (C$_8$) | 4.2 | 5.6 | 6.3 | 6.1 |
| EB | 25.7 | 22.6 | 19.7 | 24.5 |
| Xylene | 64.2 | 65.3 | 68.0 | 64.4 |
| Selectivity, % | | | | |
| $\Delta$ Xylene* | 29.6 | 29.7 | 38.9 | 28.2 |
| Naphthenes (C$_8$) | 29.9 | 33.2 | 31.9 | 39.8 |
| Xylenes | 59.5 | 62.9 | 70.8 | 68.0 |
| Aromatics | 16.3 | 10.3 | 10.5 | 10.6 |
| Light Gas | 9.5 | 11.8 | 8.0 | 6.1 |
| Non-aromatics | 14.7 | 15.0 | 10.8 | 15.3 |
| Xylene Distribution, % | | | | |
| Para- | 22.1 | 24.9 | 25.8 | 21.0 |
| Meta- | 63.3 | 59.2 | 55.8 | 66.4 |
| Ortho- | 14.6 | 15.9 | 18.4 | 12.6 |

*Based on xylene gain.

EXAMPLE 3

Catalyst C was employed to isomerize a model feed that contained 40% EB and 60% m-xylene at a pressure of 150 psig and a H$_2$/HC ratio of 5. Four different runs (5 to 8) were made under varying conditions. The conditions and results are shown in Table 3 below. The xylene gain as a function of EB conversion for Runs 5, 6 and 7 are plotted in FIG. 1.

TABLE 3

| | RUN NO. | | | |
|---|---|---|---|---|
| | 5 | 6 | 7 | 8 |
| P, psig | 750 | 750 | 750 | 800 |
| WHSV (catalyst) | 15 | 8 | 4 | 8 |
| EB Conversion, % | 30.6 | 46.9 | 60.0 | 32.3 |
| Xylene Gain, wt % | 4.2 | 7.0 | 9.7 | 5.2 |
| APXE, % | 73 | 100 | 110 | 101 |
| AOXE, % | 39 | 58 | 79 | 74 |
| AEBE, % | 31 | 50 | 67 | 34 |
| B/ΔEB, molar | 0.04 | 0.04 | 0.04 | 0.14 |
| Product Distribution, wt % | | | | |
| Light Gas | 0.3 | 0.9 | 1.6 | 1.7 |
| Non-aromatics ($C_6 + C_7$) | 1.1 | 2.3 | 2.6 | 1.4 |
| Aromatics ($C_6, C_7, C_9, C_{10}$) | 1.0 | 1.2 | 1.6 | 2.3 |
| Naphthenes ($C_8$) | 5.7 | 7.4 | 8.4 | 2.4 |
| EB | 27.1 | 20.7 | 15.7 | 26.5 |
| Xylene | 64.8 | 67.5 | 70.2 | 65.8 |
| Selectivity, % | | | | |
| Δ Xylene* | 35.4 | 38.0 | 41.3 | 41.2 |
| Naphthenes ($C_8$) | 45.3 | 38.6 | 35.8 | 19.0 |
| Xylenes | 80.7 | 76.6 | 77.1 | 60.2 |
| Aromatics | 8.1 | 6.7 | 5.5 | 16.1 |
| Light Gas | 2.6 | 5.0 | 6.9 | 13.2 |
| Non-aromatics | 8.6 | 11.7 | 10.5 | 10.5 |
| Xylene Distribution, % | | | | |
| Para- | 17.3 | 23.7 | 26.0 | 23.8 |
| Meta- | 73.5 | 62.3 | 56.3 | 58.2 |
| Ortho- | 9.3 | 14.0 | 17.7 | 18.0 |

*Based on xylene gain.

Figure 1:
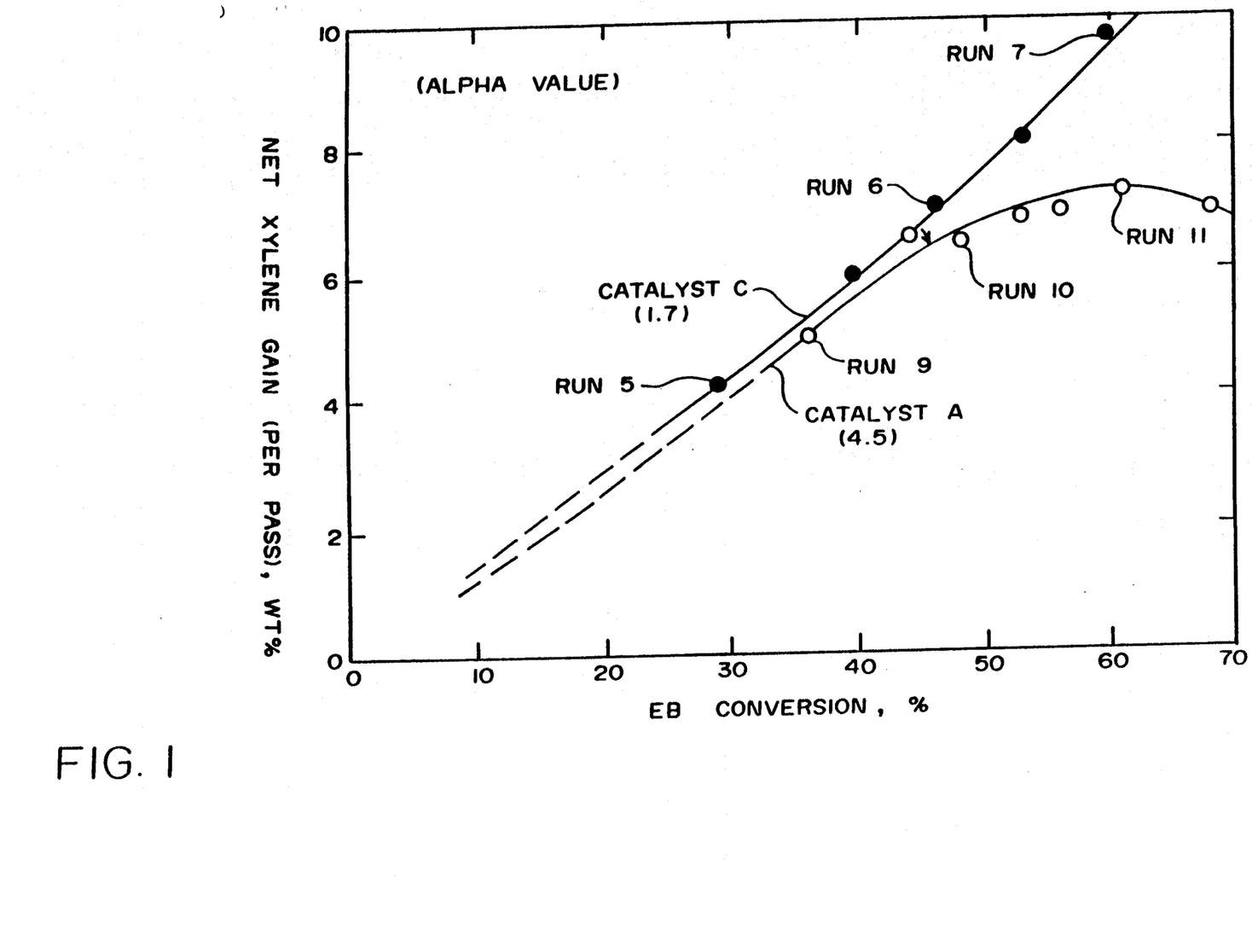
FIG. 1 is a graph showing ethyl benzene conversion versus net xylene gain for a number of the catalysts of the present invention at one set of conversion conditions.

As can be seen from the above and FIG. 1, xylene gain varied from 4 to 10 wt. % as EB conversion increased from 30 to 60%. These gains represent a 9 to 17% increase of xylenes over the xylene content of the feed.

The product distribution for Run No. 8 is set forth in more detail in the following Table 4.

TABLE 4

| | Feed | Yield, wt % | Selectivity, % |
|---|---|---|---|
| $C_8$-Hydrocarbons | | 94.7 | 58.1 |
| EB | 40 | 26.5 | — |
| Xylenes | 60 | 68.5 | 41.2 |
| Naphthenes | | 2.4 | 16.9 |
| Aromatics | 2.3 | | 18.2 |
| $C_6$ | | 1.3 | 10.2 |
| $C_7$ | | 0.5 | 41.0 |
| $C_9 + C_{10}$ | | 0.5 | 4.0 |
| Non-Aromatics | 3.0 | | 23.7 |
| $C_1 + C_2$ | | 0.4 | 3.2 |
| $C_3 + C_4$ | | 0.8 | 6.7 |
| $C_5 - C_7$ | | 1.8 | 13.8 |

The yields of $C_8$-hydrocarbons and side-products formed on a once-through basis for Run No. 8 as shown in Table 4 above are representative of the yields and side-products that can be obtained from the present invention. In general, $C_8$-aromatics and naphthenes constitute 90 to 95% of the product formed at 800° F. for about 30% ethyl benzene conversion and at least 100% APXE.

The naphthenes are principally dimethylcyclohexanes and methylethylcyclopentanes of similar yields. Small quantities of propyl- and trimethyl-cyclopentanes are also formed. These naphthenes are potential xylenes that would be recycled along with ethylcyclohexane and unconverted EB.

The low yields of benzene and diethylbenzene reflect the low selectivity of the catalysts for dealkylation and disproportionation of ethyl benzene. The dealkylation selectivity, defined as the molar ratio of benzene to converted ethyl benzene, was 0.14 at 800° F., which is a relatively small value.

Hydrodealkylation of m-xylene was the principal source of toluene. Xylene disproportionation was negligible.

EXAMPLE 4

Catalyst A was employed to isomerize a model feed that contained 40% EB and 60% m-xylene at a pressure of 150 psig and a $H_2$/HC ratio of 5. Six different runs (9 to 14) were made under varying conditions. The conditions and results are shown in Table 5 below. The xylene gain as a function of EB conversion for Runs 9, 10 and 11 are plotted in FIG. 1.

TABLE 5

| | RUN NO. | | | | | |
|---|---|---|---|---|---|---|
| | 9 | 10 | 11 | 12 | 13 | 14 |
| T, °F. | 750 | 750 | 750 | 800 | 800 | 800 |
| P, psig | 150 | 150 | 150 | 150 | 200 | 200 |
| WHSV (catalyst) | 18 | 10 | 8 | 11 | 18 | 15 |
| EB Conversion, % | 36.9 | 49.2 | 61.8 | 38.3 | 41.6 | 48.3 |
| Xylene Gain, wt % | 5.0 | 6.4 | 7.5 | 4.5 | 4.4 | 6.7 |
| APXE, % | 99 | 107 | 106 | 105 | 103 | 104 |
| AOXE, % | 66 | 83 | 86 | 91 | 82 | 86 |
| AEBE, % | — | 53 | — | 40 | — | — |
| B/ΔEB, molar | 0.08 | 0.07 | 0.08 | 0.23 | 0.18 | 0.15 |
| Product Distribution, wt % | | | | | | |
| Light Gas | 1.7 | 3.1 | 5.7 | 3.8 | 4.4 | 4.6 |
| Non-aromatics ($C_6 + C_7$) | 1.9 | 2.3 | 3.3 | 0.9 | 2.2 | 2.1 |
| Aromatics ($C_6, C_7, C_9, C_{10}$) | 1.7 | 2.0 | 2.5 | 3.8 | 3.5 | 3.5 |
| Naphthenes ($C_8$) | 4.5 | 5.4 | 5.6 | 2.0 | 2.2 | 2.3 |
| EB | 24.7 | 19.5 | 14.9 | 23.7 | 22.8 | 20.2 |
| Xylene | 65.5 | 67.8 | 68.1 | 65.9 | 64.9 | 67.3 |
| Selectivity, % | | | | | | |
| Δ Xylene* | 34.3 | 33.9 | 31.2 | 30.6 | 26.8 | 35.5 |
| Naphthenes ($C_8$) | 29.3 | 28.4 | 21.8 | 13.4 | 13.4 | 12.2 |
| Xylenes | 63.6 | 62.3 | 53.0 | 44.0 | 40.2 | 47.7 |
| Aromatics | 12.0 | 10.0 | 10.4 | 25.2 | 19.6 | 17.2 |
| Light Gas | 11.6 | 16.1 | 23.5 | 25.5 | 27.5 | 24.2 |
| Non-aromatics | 12.8 | 11.6 | 13.1 | 5.3 | 12.7 | 10.9 |
| Xylene Distribution, % | | | | | | |

TABLE 5-continued

| | RUN NO. | | | | | |
|---|---|---|---|---|---|---|
| | 9 | 10 | 11 | 12 | 13 | 14 |
| Para- | 23.4 | 25.3 | 25.0 | 24.8 | 24.3 | 24.6 |
| Meta- | 60.8 | 54.8 | 54.3 | 53.2 | 55.5 | 54.4 |
| Ortho- | 15.8 | 19.9 | 20.7 | 22.1 | 20.1 | 21.0 |

*Based on xylene gain.

EXAMPLE 5 and a WHSV (catalyst) of 6 to 18. The results for Run Nos. 15 to 22 are shown in Table 7 below.

TABLE 7

Ultimate Xylene Yield and Selectivity at 750° F.: Upper Limit[a]

| | Run No. | | | | | | | |
|---|---|---|---|---|---|---|---|---|
| | 15 | 16 | 17 | 18 | 19 | 20 | 21 | 22 |
| | Feed | | | | | | | |
| % EB | 100 | | | 40 | | | 25 | |
| % m-Xylene | 0 | | | 60 | | | 75 | |
| EB Conversion, % | 56 | 66 | 37 | 49 | 57 | 69 | 33[b] | 37[b] |
| Yield, wt % | | | | | | | | |
| Xylene | 69 | 69 | 86 | 85 | 82 | 78 | 86 | 83 |
| Other Aromatics | 10 | 10 | 5 | 4 | 4 | 4 | 5 | 6 |
| Non-aromatics | 21 | 21 | 9 | 11 | 13 | 18 | 9 | 11 |
| Selectivity, % | | | | | | | | |
| Xylene | 69 | 69 | 64 | 62 | 66 | 44 | 44 | 30 |
| Other Aromatics | 10 | 10 | 12 | 11 | 11 | 10 | 20 | 23 |
| Non-aromatics | 21 | 21 | 24 | 27 | 34 | 46 | 36 | 47 |
| Xylene Gain, wt % | 29.7 | 36.4 | 4.9 | 6.4 | 6.9 | 6.9 | 1.1 | 0.6 |
| APXE, % | 181 | 141 | 99 | 107 | 107 | 105 | 100 | 101 |
| AOXE, % | 53 | 90 | 66 | 83 | 82 | 91 | 86 | 92 |
| AEBE, % | 44 | 56 | 38 | 53 | 61 | 77 | 40 | 45 |

[a]Assumed that recycled $C_8$-naphthenes isomerize to xylenes with 100% selectivity.
[b]P = 100 psig, $H_2$/HC = 3.

The results from Examples 2 to 4 are summarized in Table 6 below to show the effect of zeolite acidity (and corresponding catalyst acidity).

TABLE 6

| | Catalyst | | | |
|---|---|---|---|---|
| | G | | C | A |
| | Run No. | | | |
| | 1 | 4 | 8 | 12 |
| Alpha (Catalyst) | | 0.05 | 0.85 | 2.2 |
| Alpha Zeolite | | 0.1 | 1.7 | 4.5 |
| T, °F. | 800 | 800 | 800 | 800 |
| P, psig | 200 | 250 | 150 | 150 |
| WHSV (catalyst) | 2 | 3 | 8 | 11 |
| EB Conversion % | 36 | 39 | 32 | 38 |
| Xylene Gain, wt % | 4.2 | 4.4 | 5.2 | 4.5 |
| APXE, % | 94 | 89 | 101 | 105 |
| B/ΔEB, molar | 0.04 | 0.04 | 0.14 | 0.23 |
| Selectivity, % | | | | |
| Δ Xylene* | 29.6 | 28.2 | 41.2 | 30.6 |
| $C_8$-Naphthenes | 29.9 | 39.8 | 19.0 | 13.4 |
| Xylene | 59.5 | 68.0 | 60.2 | 44.0 |
| Other Aromatics | 16.3 | 10.6 | 16.1 | 25.2 |
| Non-aromatics | 24.2 | 21.4 | 23.7 | 30.8 |

*Based on net xylene gain.

As can be seen from the above results and FIG. 1, zeolite alphas of from about 0.1 to about 5 (with corresponding alphas of the composite catalyst of about 0.05 to about 2.5) lead to acceptable levels of catalyst activity for ethyl benzene with a net xylene gain.

EXAMPLE 6

Catalyst A was employed to isomerize three different feeds containing 25, 40 and 100% ethyl benzene (EB) respectively at various EB conversions at a temperature of 750° F., a pressure of 150 psig, an $H_2$/HC ratio of 5, As can be seen from the above results, isomerization of EB resulted in the formation of para-rich xylenes. As a consequence, the xylenes obtained with a mixed feed contained more than an equilibrium quantity of the para-isomer over a range of conversions. This behavior is attributable to restricted diffusion of the comparatively large $C_8$-naphthenic intermediates in the pores of ZSM-5. Although theory indicates that the observed rate of the EB isomerization would be lower than the intrinsic rate because of the diffusional constraint, the effect in this case had the advantage of compensating for the low xylene isomerization activity of the catalysts.

EXAMPLE 7

A model feed containing 40% EB and 60% m-xylene was isomerized at a temperature of 750° F., a pressure of 150 psig and an $H_2$/HC ratio of 5 with Catalysts A and A-1. The results of the isomerization for each catalyst are shown below in Table 8.

TABLE 8

| | Catalyst | |
|---|---|---|
| | A-1 | A |
| DA (catalyst) | 25 | 50 |
| Alpha (catalyst) | 2.2 | 2.2 |
| % Pt-on-$Al_2O_3$ | 0.18 | 0.3 |
| WHSV (catalyst) | 10 | 10 |
| EB Conversion % | 49 | 49 |
| Xylene Gain, wt % | 2.0 | 6.4 |
| APXE, % | 105 | 107 |
| B/ΔEB, molar | 0.10 | 0.07 |
| Selectivity, %[a] | | |
| Δ Xylene[b] | 10.6 | 33.9 |
| $C_8$-Naphthenes | 27.9 | 28.4 |
| Xylene | 38.5 | 62.3 |
| Aromatics ($C_6$, $C_7$, $C_9^+$) | 10.4 | 10.0 |
| Light Gas | 24.8 | 16.1 |

TABLE 8-continued

| | Catalyst | |
|---|---|---|
| | A-1 | A |
| Non-aromatics ($C_6^+$) | 26.3 | 11.6 |

[a] Upper limit.
[b] Based on net xylene gain.

As can be seen from the above results at constant acidity, an increase of DA from 25 to 50 results in a decrease of hydrocracking.

EXAMPLE 8

A model feed containing 40% EB and 60% m-xylene was isomerized at 800° F. at a pressure of 150 psig with a $H_2/HC$ ratio of B with Catalysts C and C-1. The results of the isomerization for each catalyst are shown below in Table 9.

TABLE 9

| | Catalyst | |
|---|---|---|
| | C | C-1 |
| DA (catalyst) | 50 | 90 |
| Alpha (catalyst) | 0.85 | 0.85 |
| Alpha (Zeolite) | 1.7 | 1.7 |
| % Pt-on-$Al_2O_3$ | 0.3 | 0.6 |
| WHSV (catalyst) | 8 | 8 |
| EB Conversion, % | 32 | 30 |
| Xylene Gain, wt % | 5.2 | 4.4 |
| APXE, % | 101 | 99 |
| B/ΔEB, molar | 0.14 | 0.12 |
| Ultimate Yield,[a] wt % | | |
| Xylene | 84–80 | 84–78 |
| Aromatics | 7–9 | 6–9 |
| Light Gas | 5–6 | 4–5 |
| Non-aromatics ($C_6^+$) | 4–5 | 6–8 |
| Selectivity[a] % | | |
| Δ Xylene[b] | 41–49 | 35–47 |
| Naphthenes ($C_8$) | 17– | 25– |
| Xylene | 58–49 | 60–47 |
| Aromatics | 19–22 | 15–20 |
| Light Gas | 13–16 | 10–13 |
| Non-aromatics ($C_6^+$) | 10–13 | 15–20 |

[a] Upper and lower limits.
[b] Based on net xylene gain.

As can be seen from the above results, at constant acidity, an increase of DA from 50 to 90, achieved with a 0.6% Pt/$Al_2O_3$ component, did not change the ultimate xylene yield. The increase of Pt content should be beneficial to cycle length and to ultimate life of the catalyst.

EXAMPLE 9

A model feed containing 40% EB and 60% m-xylene was isomerized at 750° F. and 150 psig with a $H_2/HC$ ratio of 5 with the steamed Catalysts B and B-1, each containing 20% HZSM-5 having a crystal size of about 0.03 microns, but differing in their dehydrogenation activity. The results of the isomerization for each catalyst are shown below in Table 10.

TABLE 10

| | Catalyst | |
|---|---|---|
| | B | B-1 |
| DA (catalyst) | 50 | 80 |
| Alpha (catalyst) | 2.2 | 2.2 |
| Alpha (Zeolite) | 11 | 11 |
| WHSV (catalyst) | 12 | 15 |
| EB Conversion, % | 33 | 34 |
| Xylene Gain, wt % | 2.5 | 2.7 |
| APXE, % | 93 | 95 |
| B/ΔEB, molar | 0.06 | 0.09 |

TABLE 10-continued

| | Catalyst | |
|---|---|---|
| | B | B-1 |
| Ultimate Yield, wt % | | |
| Xylene | 88–76 | 83–73 |
| Aromatics | 3–6 | 4–6 |
| Light Gas | 4–9 | 9–14 |
| Non-aromatics ($C_6^+$) | 5–9 | 4–7 |
| Selectivity,[a] % | | |
| Δ Xylene[b] | 19–39 | 20–32 |
| Naphthenes ($C_8$) | 51– | 37– |
| Xylene | 70–39 | 57–32 |
| Aromatics | 7–14 | 10–15 |
| Light Gas | 11–23 | 22–35 |
| Non-aromatics ($C_6^+$) | 12–24 | 11–18 |

[a] Upper and lower limits.
[b] Based on net xylene gain.

As can be seen from the above, with a steamed catalyst containing 20% steamed HZSM-5 (α=11.2), an increase of DA from 50 to 80 brought about an increase in hydrocracking. The results demonstrate that when the zeolite alpha value greatly exceeds about 5, a large increase of hydrogenation activity will lead to noticeable increase of hydrocracking.

EXAMPLE 10

A model feed containing 40% EB and 60% m-xylene was isomerized at 750° F. at a pressure of 150 psig and an $H_2/HC$ ratio of 5 with Catalysts A and A-2. The results of the isomerization for each catalyst are shown below in Table 11.

TABLE 11

| | Catalyst | |
|---|---|---|
| | A | A-2 |
| Alpha (catalyst) | 4.5 | 4.5 |
| DA | 50 | — |
| Pt-Dispersion[a] | 1 | 0.15 |
| WHSV (ZSM-5) | 36 | 20 |
| EB Conversion, % | 37 | 38 |
| Xylene Gain, wt % | 5.0 | 1.2 |
| APXE, % | 99 | 98 |
| B/ΔEB, molar | 0.08 | 0.14 |
| Selectivity, % | | |
| Xylene | 64 | 45 |
| Other Aromatics | 12 | 18 |
| Non-Aromatics | 24 | 37 |

[a] Determined by chemisorption.

As can be seen from the above Table 11, Catalyst A-2, which comprises Pt impregnated on high silica HZSM-5, was inferior to Catalyst A comprised of a physical mixture of a zeolite component and a metal component in the form of a reforming catalyst. The reason for this was low dispersion of Pt on the zeolite in Catalyst A-2.

EXAMPLE 11

The high silica ($SiO_2/Al_2O_3=2200$) HZSM-5 Catalyst A and the steamed HZSM-5 Catalyst B of the present invention were employed to isomerize a model feed that contained 40 wt. % ethyl benzene and 60 wt. % m-xylene. Isomerization was performed at a temperature of 750° F., a pressure of 150 psig, and an $H_2/HC$ ratio of 5/1.

The results obtained from these isomerizations and the predicted ultimate xylene yields at extinction obtainable by isomerizing are shown in Table 12 below.

TABLE 12

|  | Catalyst A | Catalyst B |
|---|---|---|
| Acidity of Catalyst, alpha value | 2.2 | 2.2 |
| Acidity of Zeolite, alpha value | 4.5 | 11 |
| $SiO_2/Al_2O_3$ of Zeolite | 2200 | 55 |
| Percent of Zeolite in Catalyst | 50 | 20 |
| WHSV (catalyst) | 18 | 12 |
| EB-conversion, % | 37 | 33 |
| Net Xylene Gain, wt. % | 5.0 | 2.5 |
| APXE, % | 99 | 93 |
| Benzene/$\Delta$EB, mole/mole | 0.1 | 0.1 |
| Predicted Ultimate Yield, Wt. % | | |
| Xylene | 86–80 | 88–76 |
| Other Aromatics ($C_6$–$C_7$, $C_9$–$C_{10}$) | 5–7 | 3–6 |
| Non-Aromatics ($C_1$–$C_7$) | 9–13 | 9–18 |

The above results shows that Catalyst B, which contains HZSM-5 ($SiO_2/Al_2O_3=55$, $\alpha=11$) that has not been steamed too severely, is an acceptable alternative to a catalyst containing as a zeolite a high silica form of lower alpha activity, provided that the overall catalyst alpha does not greatly exceed a value of about 2. The slightly lower xylene yield produced by Catalyst B and the lower activity of the Catalyst B, when compared to the results for Catalyst A, are differences that can be compensated for by the use of a slightly higher operating temperature.

EXAMPLE 12

This Example illustrates the dependence of xylene gain and predicted ultimate yield on the ethyl benzene (EB)-content of the feed.

In this Example, two different feeds were treated with Catalyst A, one feed having an EB content of 25% and the other an EB content of 40. The feeds were reacted at a temperature of 750° F., a pressure of 100 psig and an $H_2$/HC ratio of 3/1. The EB conversion was 33% and WHSV (catalyst) was 10. The results are shown in Table 13 below.

TABLE 13

|  | Feed | |
|---|---|---|
| EB, wt. % | 25 | 40 |
| m-xylene, wt. % | 75 | 60 |
| Xylene Gain, wt. % | 1.1 | 4.7 |
| APXE, %[a] | 100 | 104 |
| Predicted Ultimate Yields, wt. %[a] | | |
| Xylene | 86–80 | 81–78 |
| Aromatics ($C_6$, $C_7$, $C_9$, $C_{10}$) | 5–7 | 8–9 |
| Non-aromatics ($C_1$–$C_7$) | 9–13 | 11–13 |

[a]Upper and lower limits.

The above results demonstrate that the catalysts of the preset invention are sufficiently selective for the product of a net xylene gain even with feeds that contain considerably less than 40% EB.

EXAMPLE 13

The high silica ($SiO_2/Al_2O_3=6000$) HZSM-5 Catalyst C and the sodium exchanged NaHZSM-5 Catalyst D were employed to isomerize a model feed that contained 40 wt. % EB and 60 wt. % m-xylene. Isomerization was performed at a temperature of 800° F., a pressure of 150 psig and an $H_2$/HC ratio of 5/1. For comparison, an impregnated, steamed commercial HZSM-5 Catalyst E having a low dehydrogenation activity (DA) of 2.7 and a high acidity shown by an alpha value of 10 was employed to isomerize the feed at the same conditions. The results are shown in Table 14 below.

TABLE 14

|  | Catalyst C | Catalyst D | Catalyst E |
|---|---|---|---|
| Zeolite, wt. % | 50% HZSM-5 | 50% NaHZSM-5 | 50% HZSM-5[a] |
| Zeolitic, $SiO_2/Al_2O_3$-Ratio | 6000/1 | 70/1 | 70/1 |
| Metal Component, wt. % | 50% of Pt/$Al_2O_3$ (0.3% Pt) | 50% of Pt/$Al_2O_3$ (0.3% Pt) | 0.1% Pt[b] |
| Gamma Alumina, wt. % | 0 | 0 | 50% |
| Acidity of Catalyst, Alpha Value | 0.85 | 0.01 | 10 |
| Acidity of Zeolite, Alpha Value | 1.7 | 0.02 | 20 |
| Dehydrogenation Activity of Catalyst | 50 | 50 | 2.7 |
| WHSV (catalyst) | 8 | 3 | 10 |
| EB-Conversion, % | 32 | 31 | 37 |
| Net Xylene Gain, wt. % | 5.2 | 2.5 | 0 |
| APXE, % | 101 | 101 | 101 |
| Benzene/$\Delta$EB, mole/mole | 0.1 | 0.2 | 0.5 |
| Ultimate Yield, wt. % | | | |
| Xylene | 84–80 | 72–69 | 62–60 |
| Benzene | 4–5 | 6–7 | 13–15 |
| Other Aromatics ($C_7$, $C_9$, $C_{10}$) | 3–4 | 5–5 | 6–6 |
| Light Gas ($C_1$–$C_5$) | 5–6 | 14–16 | 12–12 |
| Non-Aromatics ($C_6$, $C_7$) | 4–5 | 3–3 | 7–7 |

[a]Steamed to reduce acidity.
[b]Pt impregnated on the composited catalyst.

A comparison of the results of Catalyst C with those of Catalyst D show that the hydrogen form of Catalyst C is preferred over an alkali-exchanged form such as in Catalyst D. The sodium-exchanged form of HZSM-5 ($SiO_2/Al_2O_3=70$) of Catalyst D is a less satisfactory zeolitic component by reason of its high cracking selectivity, which was excessive even at a zeolite alpha value of 0.02.

Figure 2:
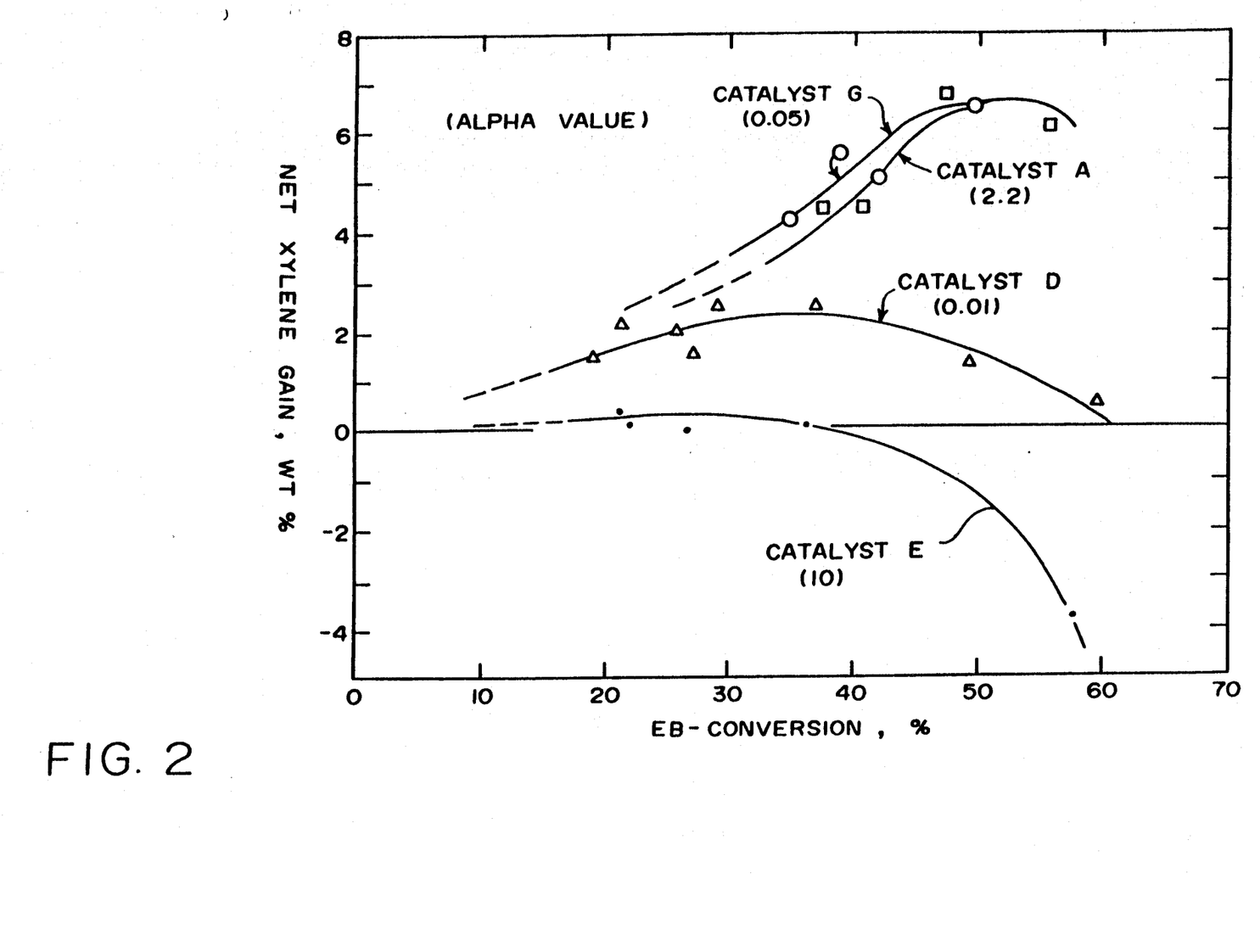
FIG. 2 is a graph showing ethyl benzene conversion versus net xylene gain for a number of catalysts of the present invention at a different set of catalyst conditions.

The above isomerization tests are repeated at varying EB conversions for the high silica Catalysts A and G, the sodium exchanged Catalyst D and the Comparison Catalyst E, and the results are plotted in FIG. 2. FIG. 2 also shows that the hydrogen form of Catalysts A and G is preferred over an alkali exchanged form such as Catalyst D.

Also, the data in FIG. 2 for the high silica catalysts define the broad range of useful catalyst acidities for the HZSM-5 catalyzed hydroisomerization of EB.

The comparative performance of the commercial Catalyst E is illustrated by the data presented in FIG. 2 and the above Table 14. The results confirm a basic conclusion of the investigations of the present invention that states that excessive hydrocracking and EB dealkylation will occur at the expense of reduced xylene yield when the catalyst acidity exceeds an alpha value of about 2 and the dehydrogenation activity falls below 10 (based on dehydrogenation of cyclohexane to benzene at 600° F).

EXAMPLE 14

The HZSM-5 Catalyst A and the larger pore HZSM-12 Catalyst F were used to treat a feed comprised of 40 wt. % EB and 60 wt. % m-xylene at a temperature of 800° F., a pressure of 150 psig, and a ratio $H_2$/HC ratio of 5/1. The results are shown in the following Table 15.

TABLE 15

| Zeolite | Catalyst A | Catalyst F |
| --- | --- | --- |
| Zeolite Acidity, Alpha Value | 4.5 | 4.6 |
| WHSV (catalyst) | 11 | 11 |
| EB-Conversion, % | 38 | 28 |
| Xylene Gain, wt. % | 4.5 | 2.1 |
| APXE, % | 105 | 100 |
| Moles Benzene/mole ΔEB | 0.23 | 0.14 |
| Selectivity, %$^a$ | | |
| Xylene | 43 | 30 |
| Aromatics | 26 | 45 |
| $C_6$ | 17 | 10 |
| $C_7$ | 3 | 14 |
| $C_{9+10}$ | 6 | 21 |
| Non-Aromatics ($C_7-$) | 31 | 25 |
| Ultimate Yield, wt. %$^a$ | | |
| Xylene | 78 | 73 |
| Aromatics ($C_6$, $C_7$, $C_9$, $C_{10}$) | 10 | 17 |
| Non-Aromatics ($C_1-C_7$) | 12 | 10 |

$^a$Upper limit.

In comparison with HZSM-5 of the same alpha value and same $SiO_2/Al_2O_3$-ratio, HZSM-12 produced lower xylene yields and higher yields of $C_9$ and $C_{10}$ aromatics as a consequence of the increased disproportionation and transalkylation of xylenes, as shown above. It also produced lower yields of non-aromatics. The lower APXE reflects a lower production of para-rich xylenes by their isomerization of EB, and not necessarily a lower intrinsic activity for xylene isomerization, in comparison to HZSM-5.

EXAMPLE 15

Catalyst C was employed to treat a paraffin feed having the following composition in weight %:
36.6 EB
56.7 xylenes
3.3 iso-octane
3.2 n-nonane
0.2 toluene.

The conditions of the reaction were temperature at 815° F., pressure at 150 psig, and an $H_2/HC$ ratio of 5/1/.

The EB conversion was 33%, the WHSV (catalyst) was 4, and the APXE was 100%. The conversion of n-nonane was 99%, and the conversion of iso-octane was 75%.

This example, thus, illustrates the ability of the catalyst of the present invention to crack normal and branched paraffins.

It will be understood that the above description of the present invention is susceptible to various modifications, changes and adaptations, and the same are intended to be comprehended within the meaning and range of equivalents of the appended claims.

What is claimed is:

1. A process for isomerizing a feed containing an aromatic $C_8$ mixture of ethyl benzene and xylene by contacting the feed, under conversion conditions with a catalyst comprising:
   (a) a crystalline aluminosilicate zeolite having a low acid activity as measured by an alpha value of from about 0.02 to about 11, an average crystal size of not more than about 0.4 microns for at least 50% by weight of the crystals, a silica to alumina ratio of at least about 12, a constraint index of about 1 to 12, and, a xylene sorption capacity greater than 1 gram per 100 grams of zeolite and an ortho-xylene sorption time for 30 percent of said capacity less than 10 minutes, said sorption capacity and sorption time being measured at 120° C. and a xylene pressure of 4.5±0.8 mm of mercury, and
   (b) a supported metal of Group VIII of the Periodic Table having a high hydrogenation/dehydrogenation activity to provide the catalyst with a dehydrogenation activity of at least 10, and
   (c) the catalyst having an acid activity as measured by an alpha value of 0.005 to 3.

2. The process according to claim 1, wherein the conversion is at a temperature between 700° and 900° F., a pressure between 100 and 1000 psig, using a feed weight hourly space velocity between 1 and 50.

3. The process according to claim 1, wherein the acid activity of the catalyst is from about 0.05 to about 2.5 alpha.

4. The process according to claim 1, wherein the zeolite has an alpha of from about 0.1 to 5.

5. The process according to claim 1, wherein the catalyst has a dehydrogenation activity of from 25 to 200.

6. The process according to claim 1, wherein the catalyst has a dehydrogenation activity of from 25 to 100.

7. The process according to claim 1, wherein the metal content of the catalyst is from 0.05 to 1.0 wt. percent based on the weight of the catalyst.

8. The process according to claim 1, wherein the zeolite is ZSM-5.

9. The process according to claim 8, wherein the ZSM-5 is predominantly in the hydrogen form.

10. The process according to claim 1, wherein the zeolite has a silica to alumina ratio of 50 to 100,000.

11. The process according to claim 1, wherein said average crystal size is from about 0.2 microns to 0.4 microns.

12. The process according to claim 1, wherein said average crystal size is from about 0.01 microns to 0.05 microns.

* * * * *